(12) United States Patent
Georgeson et al.

(10) Patent No.: US 7,312,608 B2
(45) Date of Patent: Dec. 25, 2007

(54) SYSTEMS AND METHODS FOR INSPECTING ELECTRICAL CONDUCTIVITY IN COMPOSITE MATERIALS

(75) Inventors: Gary E. Georgeson, Federal Way, WA (US); Joseph L. Hafenrichter, Bellevue, WA (US); Everett A. Westerman, Auburn, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 11/266,052

(22) Filed: Nov. 3, 2005

(65) Prior Publication Data

US 2007/0096751 A1    May 3, 2007

(51) Int. Cl.
*G01N 27/82* (2006.01)
*G01R 31/08* (2006.01)
(52) U.S. Cl. .................. 324/240; 324/238; 324/525
(58) Field of Classification Search ................ 324/234, 324/691, 237, 238, 240, 525
See application file for complete search history.

(56) References Cited

U.S. PATENT DOCUMENTS

| | | | |
|---|---|---|---|
| 4,207,520 A * | 6/1980 | Flora et al. ................. 324/238 |
| 4,706,020 A * | 11/1987 | Viertl et al. ................. 324/238 |
| 4,747,310 A * | 5/1988 | Collins et al. ................. 73/661 |
| 5,195,046 A | 3/1993 | Gerardi et al. |
| 5,202,641 A | 4/1993 | Unvala |
| 5,374,011 A | 12/1994 | Lazarus et al. |
| 5,665,913 A | 9/1997 | Chung |
| 5,841,031 A | 11/1998 | Chung |
| 6,031,212 A | 2/2000 | Westerman et al. |
| 6,270,603 B1 | 8/2001 | Westerman et al. |
| 6,613,169 B2 | 9/2003 | Georgeson et al. |
| 6,636,037 B1 * | 10/2003 | Ou-Yang ................. 324/240 |
| 6,696,174 B2 | 2/2004 | Cercone et al. |
| 6,748,791 B1 | 6/2004 | Georgeson et al. |
| 6,843,130 B2 | 1/2005 | Georgeson |
| 6,848,312 B2 | 2/2005 | Georgeson |
| 6,945,111 B2 | 9/2005 | Georgeson |

* cited by examiner

*Primary Examiner*—Anjan Deb
*Assistant Examiner*—Amy He
(74) *Attorney, Agent, or Firm*—Lee & Hayes, PLLC

(57) ABSTRACT

Systems and methods for inspecting electrical conductivity in composite materials having conductive structures are disclosed. In one embodiment, a system of inspecting electrical conductivity in an electrical bonding region includes a coil coupled to an alternating current source that is configured to induce a current in a conductive structure within the region. A processor is coupled to the coil that is operable to detect an impedance property value from the coil that results from the current induced in the conductive structure.

8 Claims, 6 Drawing Sheets

SYSTEMS AND METHODS FOR INSPECTING ELECTRICAL CONDUCTIVITY IN COMPOSITE MATERIALS

FIELD OF THE INVENTION

This invention relates generally to systems and methods for inspecting composite materials having a conductive structure, and more specifically, to systems and methods for inspecting an electrical bonding region that couples adjoining composite materials.

BACKGROUND OF THE INVENTION

Recent estimations indicate that, on the average, each airplane in the U.S. commercial aircraft fleet receives a lightning discharge about once each year. The airplane generally experiences the lightning discharge when flying through a heavily charged portion of a cloud. In such cases, the discharge generally originates at the airplane and extends outwardly from the aircraft. While the discharge is occurring, it generally moves from the nose of the airplane and onto a plurality of skin panel portions of the airplane as it moves through the charged region. The discharge may also attach to wing tips and/or edges of wing control surfaces (e.g., ailerons) during the discharge. The discharge then generally leaves the aircraft structure through the empennage. Since commercial airplanes contain relatively large amounts of potentially-explosive fuel, and also generally include sensitive electronic equipment such as navigational computers and communications equipment that may be easily damaged by a lightning discharge, commercial airplanes are required to comply with a comprehensive set of certification procedures in order to verify that the airplane is sufficiently protected from the damaging effects of a lightning discharge.

Presently, the outer skin panels in commercial airplanes are formed from an aluminum alloy, which is an excellent electrical conductor. Accordingly, by providing suitable electrical interconnections between the outer skin panels, and between other exposed portions of the aircraft structure, the current associated with the discharge is safely communicated along the skin panels and/or other structural portions as the airplane moves through the charged region. Increasingly, however, structural portions (including skin panel portions) of commercial airplanes are formed from fiber-reinforced composite materials, which are relatively poor electrical conductors. Consequently, additional conductive materials are generally incorporated into the fiber-reinforced composite materials so that adequate lightning discharge protection is achieved.

In particular, skin panels fabricated from fiber-reinforced composite materials generally include a conductive material, such as a conductive mesh, or other similar conductive structures that may be applied to surfaces of the skin panels so that the lightning current is safely communicated through the skin panels. Alternately, the conductive mesh or conductive structure may be incorporated into one or more of the layers of the skin panels.

Although the foregoing fiber-reinforced composite panels are generally sufficiently conductive, electrical conductivity must also be maintained between each of the panels in order to provide adequate lightning protection to the airplane. Accordingly, in one known method, respective edges of abutting skin panels are sanded or etched to expose edges of the conductive mesh provided in the panels. A suitably-sized and pre-assembled surface member having a conductive mesh may then is positioned on the sanded or etched portions of the abutting panels and bonded to the panels to provide electrical continuity between the abutting panels. Similarly, fiber-reinforced composite skin panels may also require a localized repair to remove a portion of the panel that has been physically damaged. The localized repair includes removing the damaged portion of the panel, and fabricating a patch that covers the removed portion. Since electrical continuity between the patch and the surrounding skin panel must be established, edge portions of the panel and the patch must be suitably prepared, which generally includes sanding or etching the edge portions, and bonding the patch to the skin panel, as described above.

To assure that suitable electrical continuity exists between the pre-assembled surface member or repair patch and the surrounding skin panel material, direct electrical conductivity measurements using a surface conductivity probe have been used. In one known method, conductivity measurements are made at various locations around the pre-assembled surface member or repair patch and suitably processed to determine if the required conductivity is attained. Although this method provides an estimation of the surface conductivity of an affected area, producing an estimation of the conductivity requires a number of independent measurements to be made by a skilled operator. Accordingly, surface conductivity measurement methods are tedious and are prone to error if not performed correctly.

SUMMARY

The present invention comprises systems and methods for inspecting electrical conductivity in composite materials having conductive structures, and in particular, to inspecting the electrical conductivity in electrical bonding regions that extend between composite materials. In one aspect, a system of inspecting electrical conductivity in an electrical bonding region includes a coil coupled to an alternating current source that is configured to induce a current in a conductive structure within the region. A processor is coupled to the coil that is operable to detect an impedance property value from the coil that results from the current induced in the conductive structure.

BRIEF DESCRIPTION OF THE DRAWINGS

Embodiments of the present invention are described in detail below with reference to the following drawings.

DETAILED DESCRIPTION

The present invention relates to systems and methods for inspecting electrical conductivity in composite materials, and in particular, to the inspection of electrical conductivity in electrical bonding regions. Many specific details of certain embodiments of the invention are set forth in the following description and in FIGS. 1 through 7 to provide a thorough understanding of such embodiments. One skilled in the art, however, will understand that the present invention may have additional embodiments, or that the present invention may be practiced without several of the details described in the following description.

Figure 1:
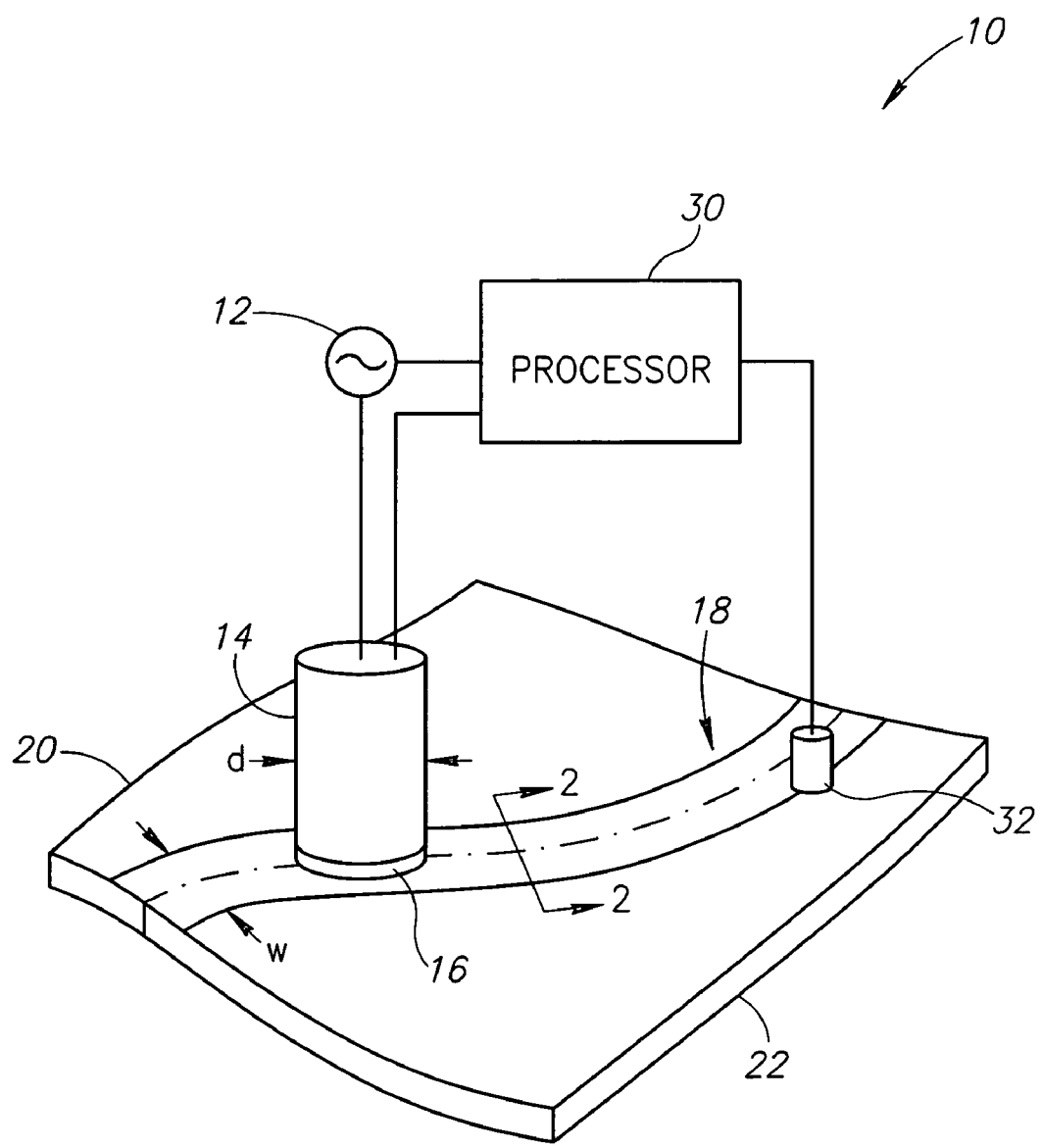
FIG. 1 is a partial schematic view of a system for inspecting an electrical bonding region, according to an embodiment of the invention.

FIG. 1 is a partial schematic view of a system 10 for inspecting an electrical bonding region, according to an embodiment of the invention. The system 10 includes an alternating current source 12 that is configured to generate an alternating current having a desired frequency. In one specific embodiment, the source 12 is configured to generate the alternating current at a frequency that ranges between approximately about 50 hertz (Hz) and approximately about 10 megahertz (MHz). In another specific embodiment, the source 12 is configured to generate the alternating current at more than a single frequency by sequentially switching from one selected frequency to other selected frequencies. In another specific embodiment, a pair of sequentially switched frequencies are generated that have a frequency ratio that ranges between approximately about 2:1 and approximately about 4:1. Inspection of the electrical bonding region with multiple frequencies advantageously provides a broader range of detection capabilities so that conductive defects at various material depths may be detected. In addition, through the use of different excitation frequencies, the signal response may be improved.

The alternating current source 12 is operatively coupled to a coil assembly 14 that is configured to generate an electromagnetic induction field that projects outwardly from a conformable base portion 16 so that eddy currents are induced in an electrical bonding region 18. The conformable base portion 16 is configured to suitably position the coil 14 over the electrical bonding region 18 so that effects stemming from surface irregularities in the region 18 may be minimized. The conformable base portion 16 will be described in greater detail below.

Figure 2:
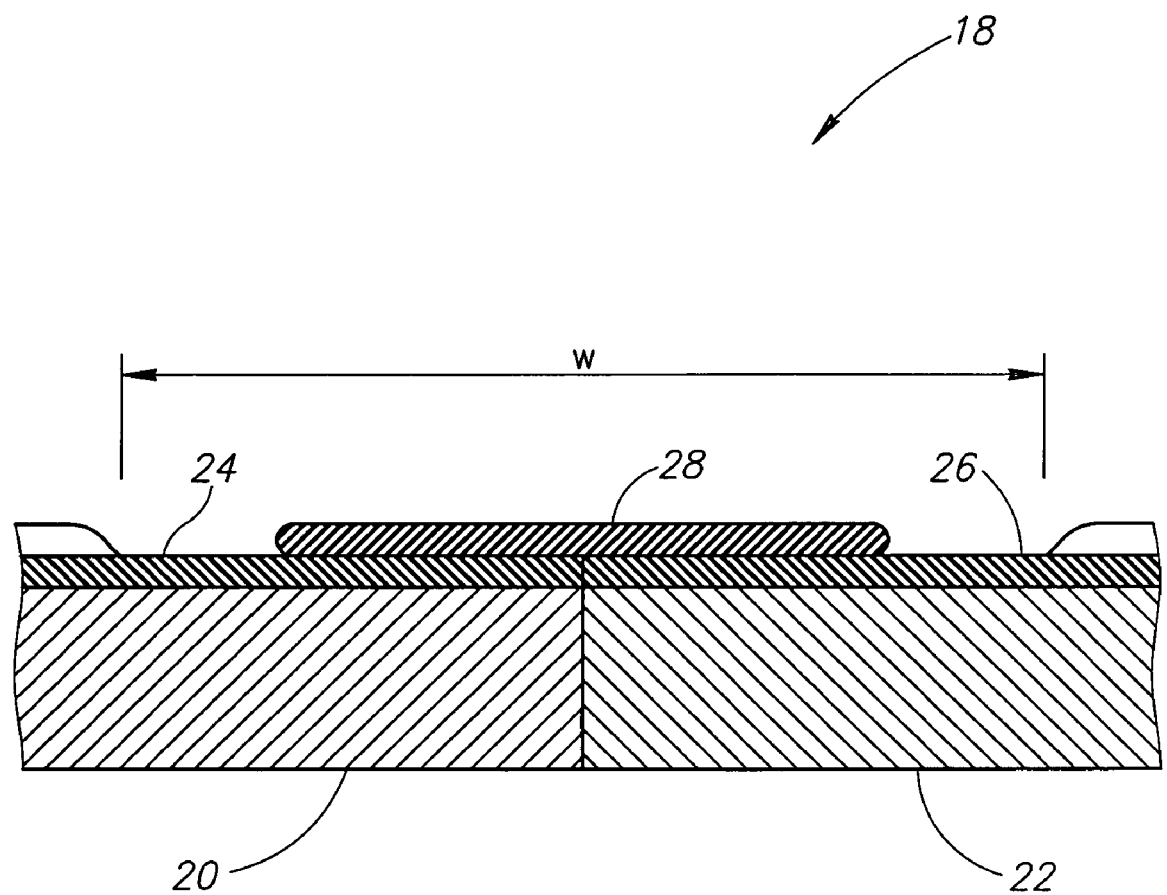
FIG. 2 is a partial cross sectional view of an electrical bonding region according to the prior art.

With reference now also to FIG. 2, the electrical bonding region 18 will now be briefly described. The bonding region 18 includes a first composite portion 20 that is proximate to a second composite portion 22. The first composite portion 20 includes a first conductive layer 24, and the second composite portion 22 includes a second conductive layer 26. The first conductive layer 24 and the second conductive layer 26 may include a metallic woven mesh that is bonded to the respective first composite portion 20 and the second composite portion 22. Alternately, the first conductive layer 24 and the second conductive layer 26 may include a metallic foil, a flame-sprayed metallic coating, a glass fabric that is coated with a metallic coating, and a metallized decal, in addition to other known conductive materials.

The electrical bonding region 18 further includes an intermediate conductive layer 28 that forms an electrically conductive path between the first conductive layer 24 and the second conductive layer 26. The intermediate conductive layer 28 may also include one of a metallic woven mesh, a metallic foil, a flame-sprayed metallic coating, a glass fabric that is coated with a metallic coating, and a metallized decal that extends onto at least a portion of the first conductive layer 24 and the second conductive layer 26. The exposed portions of the first composite portion 20, the second composite portion 22 and the intermediate conductive layer 28 extend across the first composite portion 20 and the second composite portion 22 a distance w. The first composite portion 20 and the second composite portion 22 may be covered with a suitable polymeric material (not shown) after the bonding region 18 is formed. Although FIG. 2 shows the first composite portion 20 and the second composite portion 22 in an abutting relationship, it is understood that the adjoining faces may also be suitably contoured to accept various surface patch configurations. For example, it is well known that the first composite portion 20 and the second composite portion 22 are suitably provided with corresponding stepped contours when a repair to surface portion of an aircraft is necessary. The stepped contours are generally arranged so that the steps occur on adjoining plies in the first composite portion 20 and the second composite portion 22.

Returning now in particular to FIG. 1, the coil 14 is configured to have a diameter d, and in one specific embodiment, the coil 14 has a diameter d that is approximately equal to the distance w. In another specific embodiment, the diameter d is greater than the distance w. Although the coil 14 is depicted in FIG. 1 as a generally cylindrical structure having a circular cross sectional shape, it is understood that the coil 14 may have other shapes, such as a generally rectangular cross sectional shape, or still other cross sectional shapes. In any event, the coil 14 and the alternating current source 12 are coupled to a processor 30. The processor 30 is operable to control the alternating current source 12, and to receive and process signals from the coil 14 that include a selected impedance property of the coil 14. Briefly, and in general terms, the selected impedance property value results from eddy currents induced in the electrical bonding region 18 by the coil 14 that oppose the magnetic field generated by the coil 14. Defects within the electrical bonding region 18 thus generate variations in the selected impedance property value. For example, in one specific embodiment, the selected impedance property value may include a resistance and a capacitive and/or inductive reactance, a phasor magnitude, and a phase angle. In other specific embodiments, the impedance property value may be processed so that the phasor may be graphically displayed in a complex plane. In still other particular embodiments, the processor 30 may be configured to generate phase lag information for the electrical bonding region 18, so that defects within the region 18 may be detected at various depths within the region 18. The processor 30 may also be coupled to an auxiliary coil 32 that is operable to detect an impedance property value from the electrical bonding region 18 at a location that is remote from the coil 14. The auxiliary coil 32 may also be positioned on other regions that are adjacent to the electrical bonding region 18, or even upon the region 18.

Figure 3:
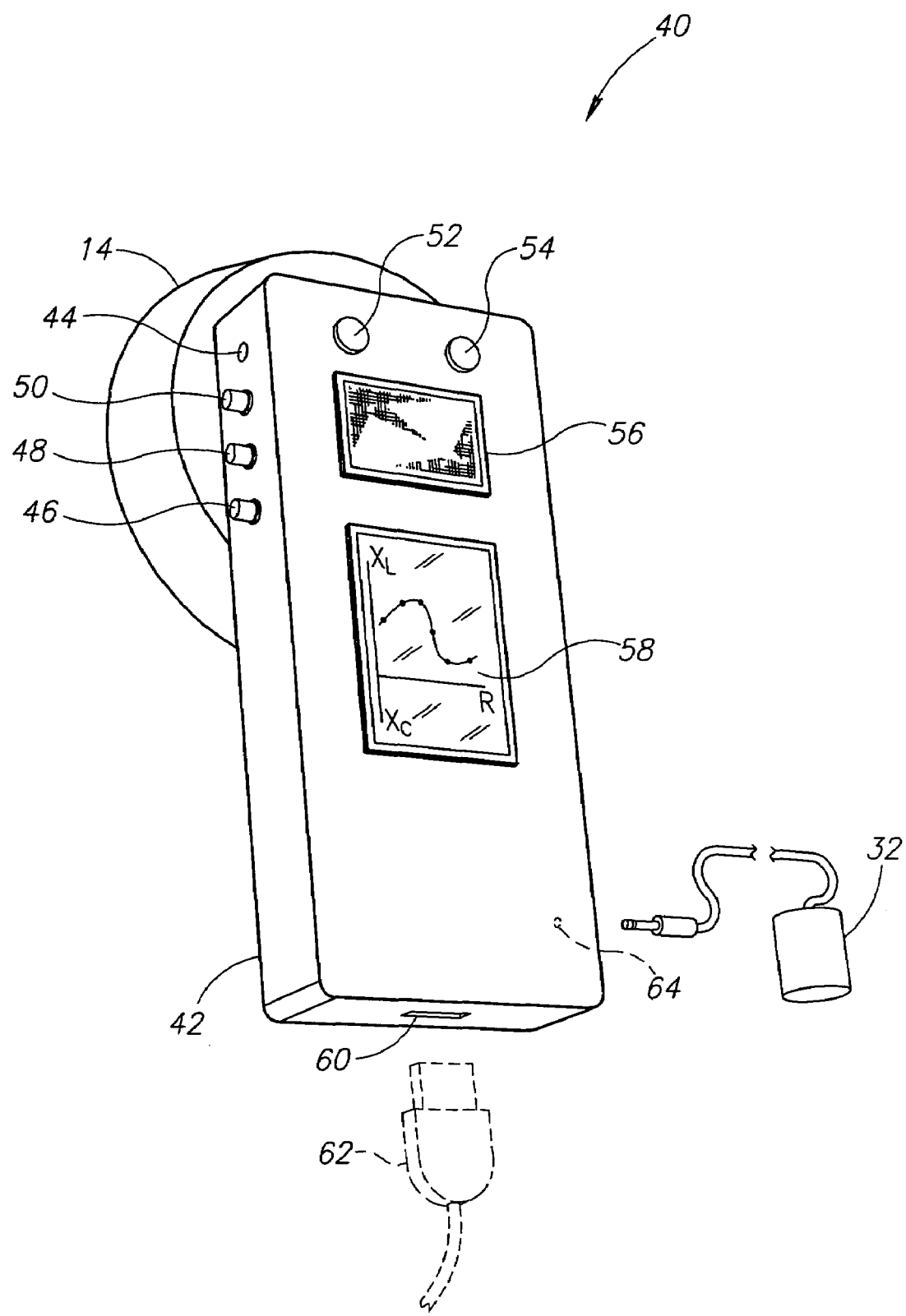
FIG. 3 is an isometric view of a hand held conductive inspection apparatus according to another embodiment of the invention.

FIG. 3 is an isometric view of a hand held apparatus 40 for inspecting an electrical bonding region, according to another embodiment of the invention. The apparatus 40 includes an outer housing 42 that is configured to be conveniently grasped and retained by a human hand. The outer housing 42 contains the processor 30 (see FIG. 1) and the alternating current source 12 (as also shown in FIG. 1), and also contains a direct current (DC) power supply that provides electrical energy to the source 12 (not shown in FIG. 3). The outer housing 42 may be fixedly coupled to the coil 14, while in another specific embodiment, the coil 14 may be selectively demountable from the outer housing 42 so that the coil 14 may be positioned adjacent to the bonding region 18, while the outer housing 42 is spaced apart from the coil 14. The apparatus 40 also includes a switch 44 that is operable to interrupt current between the DC supply and the alternating current source 12, the processor 30, and other portions of the apparatus 40 that require electrical energy. Other controls may also be provided, such as a signal amplitude level adjustment control 46 that is operable to adjustably set an amplitude of an impedance property value to a desired level, a phase adjustment control 48 that is operable to set a phase of the impedance property value to a desired level, and an alarm threshold control 50 that is operable to set an alarm level to a desired value. The amplitude level adjustment control 46, the phase adjustment control 48, and the alarm threshold control 50 will be discussed in greater detail below.

Still referring to FIG. 3, the apparatus 40 may also include a first indicator light 52 and a second indicator light 54 that are configured to provide a visual indication of an impedance property value of the electrical bonding region 18. In one specific embodiment, a selected one of the first indicator light 52 and the second indicator light 54 remains illuminated while the coil 14 is moved across the region 18, provided that a predetermined range of impedance property values is maintained. If the impedance property value changes to another value that is outside the predetermined range, the selected one of the indicator lights is extinguished, and the other is indicator light is illuminated. In another specific embodiment, the first indicator light 52 and the second indicator light 54 may include light sources having selected colors that may be used to indicate an acceptable range of impedance property values. For example, if the electrical bonding region 18 has an impedance property value that lies within a predetermined range, a selected one of the first indicator light 52 and the second indicator light 54 may be illuminated with a green color, while the other indicator light may illuminated with a red color when the impedance property value that lies outside the predetermined range.

The apparatus 40 may further include an audio annunciator 56 that is configured to emit audio tones that correspond to detected impedance property values. In one specific embodiment, the audio annunciator 56 may be configured to emit a predetermined audio tone while the apparatus 40 is detecting impedance values in the electrical bonding region 18 that lie within a predetermined range of acceptable values. In another specific embodiment, the audio tone is emitted when the apparatus 40 detects impedance property values that lie outside the range of acceptable values. In other embodiments, the audio annunciator 56 may be configured to emit a tone at a first frequency when the apparatus 40 detects impedance property values that lies within the range of acceptable values, and emits a tone at a second frequency when an impedance property value that lies outside the range of acceptable values is detected.

A display 58 may also be positioned on the apparatus 40 that is operable to visually display impedance property values detected by the apparatus 40. In one specific embodiment, the display 58 is a graphical display that is operable to display detected impedance property values. In another specific embodiment, the display 58 includes a galvanometric movement that is operable to display the detected impedance value on a calibrated scale.

The apparatus 40 may also include a data communications port 60 that may be used to communicate data acquired by the apparatus 40 to an external processor (not shown) for additional processing. Accordingly, the data communications port 60 may be configured to accept a corresponding demountable data cable 62 that couples the apparatus 40 to the external processor. The data communications port 60 may be further configured to support communications according to the universal serial bus (USB) data exchange protocol, although other protocols may be used. For example, in a specific embodiment, the IEEE-1394a data exchange protocol, known commercially as FIREWIRE, may also be used. In another specific embodiment, a serial port configured in accordance with RS-232 and RS-422 may be used. In still other embodiments, the communications port 60 may be configured as a parallel port. Alternately, the communications port 60 may be configured to communicate wirelessly with the external processor by means of wireless signals, such as radio frequency (RF) signals, infrared (IR) signals, and ultrasonic signals. The apparatus 40 may also include a connection port 64 that is configured to receive a connector, such as a plug, so that the auxiliary coil 32 may be coupled to the apparatus.

Figure 4:
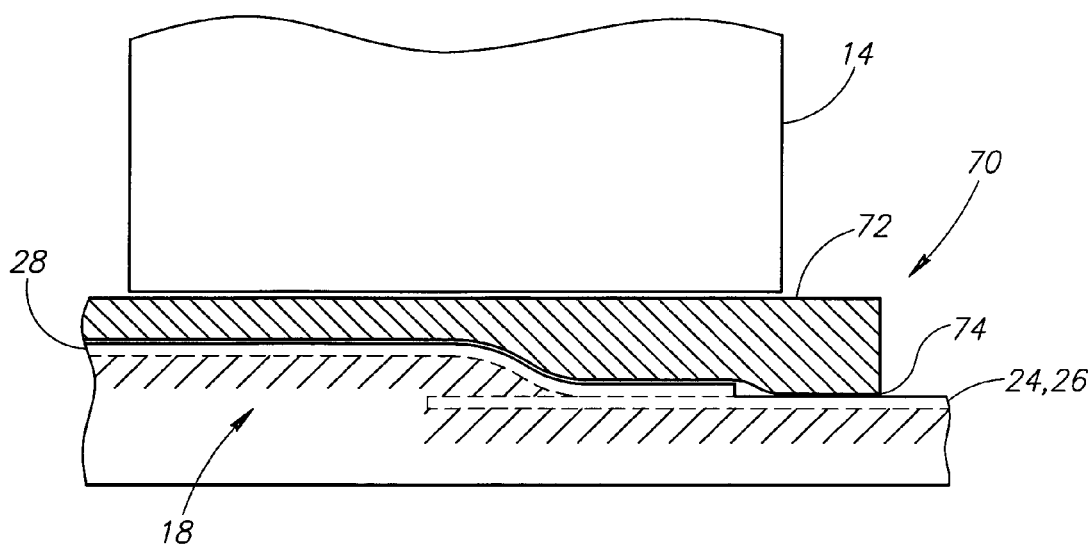
FIG. 4 is a partial cross sectional view of a conformable base portion according to another embodiment of the invention.

FIG. 4 is a partial cross sectional view of a conformable base portion 70 according to another embodiment of the invention. The base portion 70 may be formed from a compliant material such as a foamed natural or synthetic rubber, or other similar materials. The base portion 70 also includes a first surface 72 configured to abut the coil 14, and an opposing second surface 74 that readily conforms to a surface contour present in the electrical bonding region 18 when the base portion 70 is interposed between the coil 14 and the electrical bonding region 18. Accordingly, the conformable base portion 70 orients the coil 14 at a relatively consistent position relative to the electrical bonding region 18, so that more accurate impedance property measurements for the electrical bonding region 18 may be made.

Figure 5:
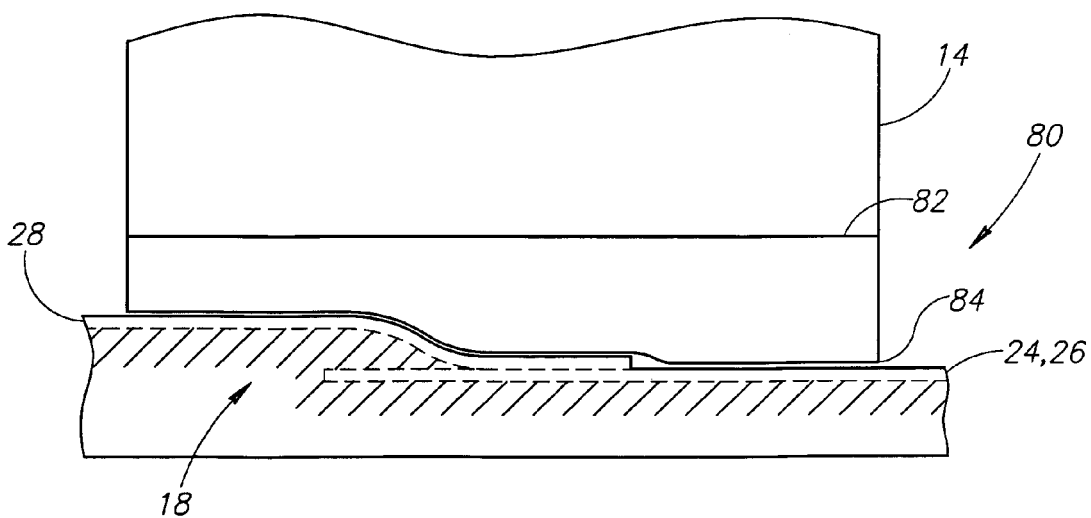
FIG. 5 is a partial cross sectional view of a conformable base portion according to still another embodiment of the invention.

FIG. 5 is a partial cross sectional view of a conformable base portion 80 according to still another embodiment of the invention. The base portion 80 may be formed from a relatively rigid polymeric material such as a formed composition rubber or a polymeric material. The base portion 80 also includes a first surface 82 configured to abut the coil 14, and an opposing second surface 84 having a predetermined shape to conform to a surface contour present in the electrical bonding region 18 when the base portion 80 is positioned on the electrical bonding region 18. The conformable base portion 80 again permits the coil 14 to be positioned relatively consistently relative to the electrical bonding region 18, so that "surface lift-off" difficulties are advantageously avoided.

Figure 6:
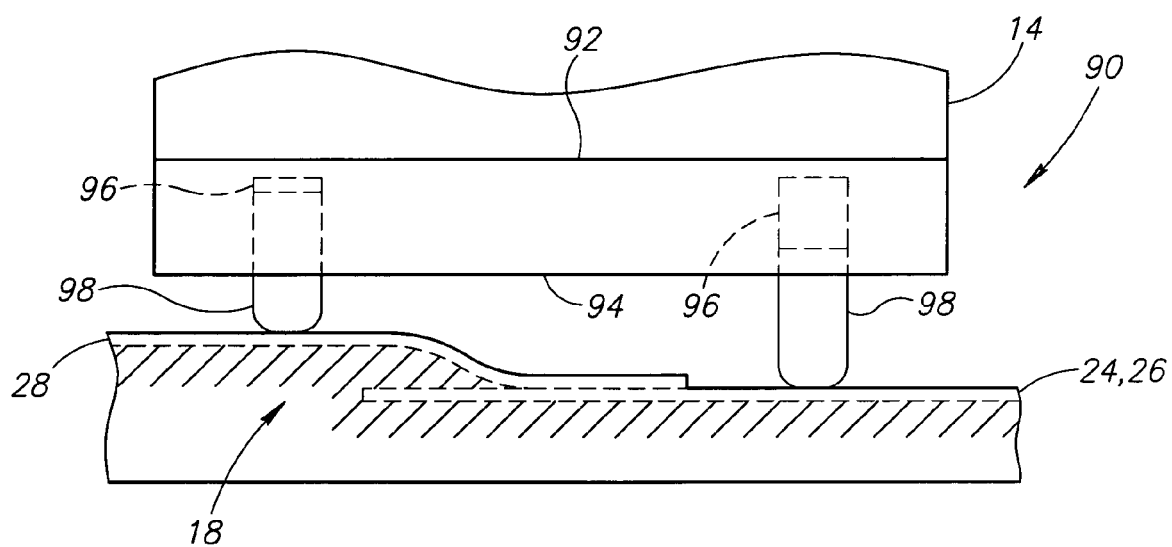
FIG. 6 is a partial cross sectional view of a conformable base portion according to still yet another embodiment of the invention.

FIG. 6 is a partial cross sectional view of a conformable base portion 90 according to still another embodiment of the invention. The base portion 90 also includes a first surface 92 configured to abut the coil 14, and an opposing second surface 94 having at least a pair of recesses 96 configured to receive legs 98 that may be adjustably positioned within the recesses 96 to extend outwardly from the second surface 94 so that the coil 14 may be suitably positioned relative to the electrical bonding region 18. Accordingly, the recesses 96 and the legs 98 may be threaded so that the base portion 90 may be suitably positioned relative to the region 18. Alternately, the recesses 96 and the legs 98 may be suitably dimensioned so that a frictional interference fit exists between each leg 98 and the corresponding recess 96.

Figure 7:
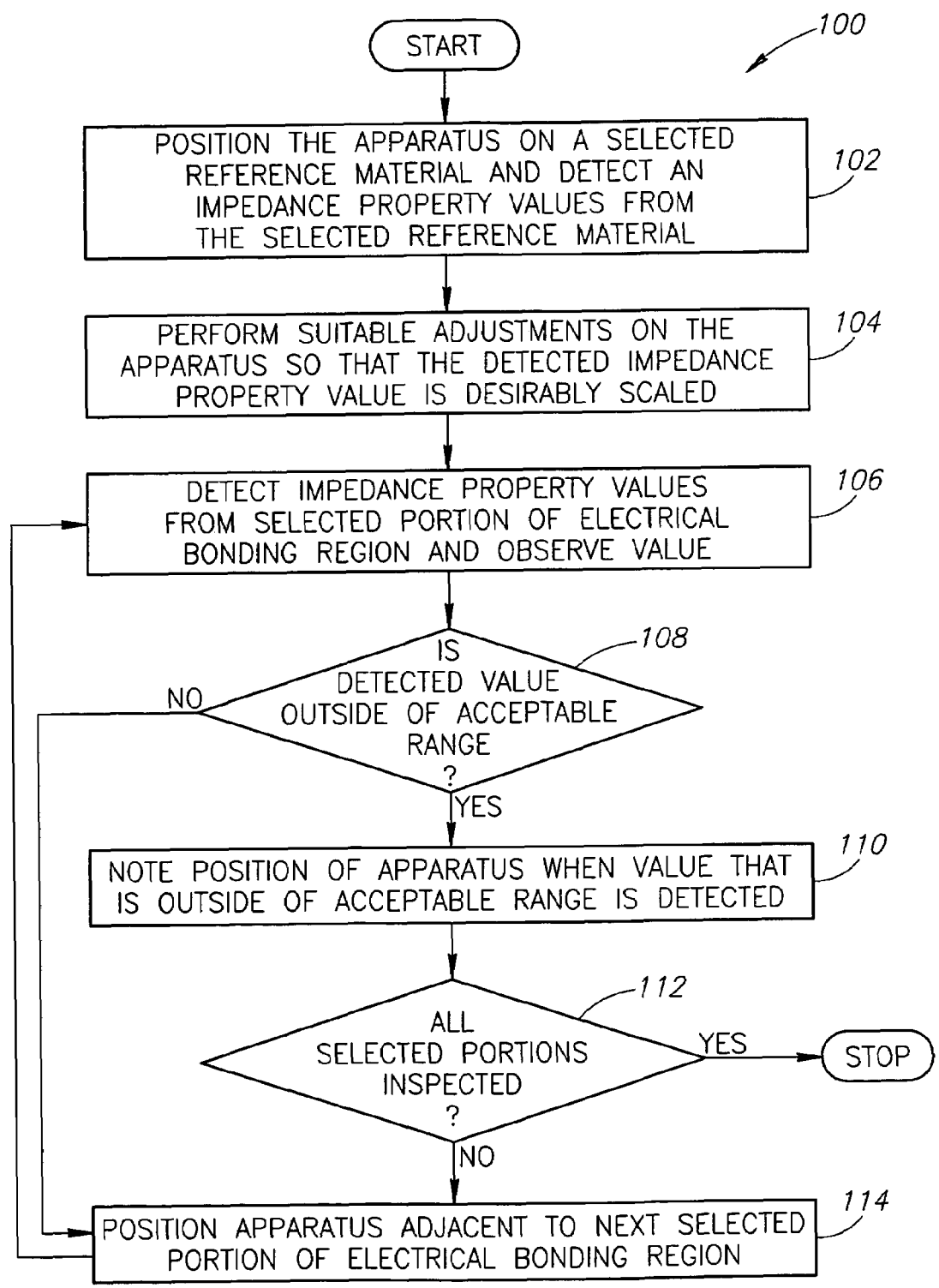
FIG. 7 is a flowchart that describes a method of inspecting an electrical bonding region according to another embodiment of the invention.

FIG. 7 is a flowchart that will be used to describe a method 100 of inspecting an electrical bonding region according to another embodiment of the invention. At block 102, an inspection apparatus, such as the embodiments described in connection with FIG. 1 and FIG. 3, is positioned on a selected reference material so that reference impedance property values may be detected. The selected reference material may include a composite panel that includes a conductive material having known impedance characteristics. Alternately, the selected reference material may include a portion of the first composite portion 20 and/or the second composite portion 22 (as shown in FIG. 2) that is sufficiently remote from the electrical bonding region 18 (as also shown in FIG. 2). The selected reference material may include a portion of the electrical bonding region 18 that is known to possess the desired impedance characteristics. In any case, the reference impedance property values may be detected by the coil 14 and/or by the auxiliary coil 32, as shown in FIG. 1 and FIG. 2. At block 104, the inspection apparatus is suitably adjusted based upon the detected reference impedance property value so that subsequent impedance property measurements are desirably scaled. Accordingly, the inspection apparatus may be adjusted to provide a desired phase angle offset, a desired magnitude for a phasor, or other suitably scaled impedance quantities. At block 106, the inspection apparatus in positioned on the electrical bonding region 18 and impedance property values are measured from the region 18. As discussed above, the impedance property values may include a resistance, a capacitive and/or inductive reactance, a phasor magnitude, and a phase angle. At block 108, if the detected impedance property value is not within an acceptable range of values, the position of the inspection apparatus is noted so that a location associated with the detected value may be identified, as shown at block 110. Alternately, if the detected impedance property value is within the prescribed range of acceptable values, other locations on the electrical bonding region 18 may be inspected by proceeding to block 114 that provides for the inspection of a next selected portion of the layer 18. If all selected portions of the layer 18 have been inspected, then the method 100 stops, as shown at block 112.

While various embodiments of the invention have been illustrated and described, as noted above, many changes can be made without departing from the spirit and scope of the invention. Accordingly, the scope of the invention is not limited by the disclosure of the various embodiments. Instead, the invention should be determined entirely by reference to the claims that follow.

What is claimed is:

1. A system of inspecting electrical conductivity, comprising:
    a coil coupled to an alternating current source and configured to induce a current in a conductive structure within the region;
    a processor coupled to the coil that is operable to detect at least an impedance property value from the coil that results from the current induced in the conductive structure;
    a conductive bonding region, the conductive bonding region further comprises a first composite portion having a first conductive layer, a second composite portion adjacent to the first composite portion and having a second conductive layer, and an intermediate conductive layer that forms an electrically conductive path extending between the first conductive layer and the second conductive layer; and
    a compliant base portion including a foamed material, the compliant base portion disposed on the coil and configured to conform to a surface contour of the conductive bonding region.

2. The system of claim 1, wherein the alternating current source further comprises a source that is operable to excite the coil at a frequency that ranges between approximately about 50 Hertz (Hz) and approximately about 10 megahertz (MHz).

3. The system of claim 1, wherein the alternating current source further comprises a source that is operable to sequentially excite the coil at more than a single frequency.

4. The system of claim 3, wherein the alternating current source further comprises a source that is operable to generate a selected pair of frequencies, further wherein the selected pair of frequencies have a frequency ratio that ranges between approximately about 2:1 and approximately about 4:1.

5. The system of claim 1, wherein the coil further comprises a diameter, and the conductive bonding region further comprises a width, further wherein the diameter is at least approximately equal to the width.

6. The system of claim 1, wherein the detected impedance property value comprises at least one of a resistance, a reactance, a phasor magnitude and a phase angle.

7. The system of claim 1, wherein the foamed material further includes one of a foamed natural rubber and a foamed synthetic rubber.

8. The system of claim 1, wherein the first conductive layer, the second conductive layer and the intermediate conductive layer are comprised of at least one of a metallic woven mesh, a metallic foil, a flame sprayed metallic coating, a fabric that is coated with a metallic coating, and a metallic decal.

* * * * *